United States Patent [19]

Bauman

[11] Patent Number: 4,694,822

[45] Date of Patent: Sep. 22, 1987

[54] SUBMERGIBLE LARYNGOSCOPE BATTERY HOUSING

[76] Inventor: Jack Bauman, 1677 San Onofre Dr., Pacific Palisades, Calif. 90272

[21] Appl. No.: 846,913

[22] Filed: Apr. 1, 1986

[51] Int. Cl.[4] ............................................. A61B 1/06
[52] U.S. Cl. .................................... 128/11; 362/158; 362/804
[58] Field of Search ......................... 128/10, 11, 6, 16; 362/158, 187, 217, 362, 804

[56] References Cited

U.S. PATENT DOCUMENTS

| 1,165,232 | 12/1915 | De Zeng |  |
|---|---|---|---|
| 2,289,226 | 7/1942 | Von Foregger | 128/16 |
| 2,433,705 | 12/1947 | Palmeter | 128/10 |
| 3,295,514 | 1/1967 | Hein et al. | 128/2.1 |
| 3,426,749 | 2/1969 | Jephcott | 128/11 |
| 3,579,269 | 5/1971 | Ostensen |  |
| 3,592,199 | 7/1971 | Ostensen | 128/6 |
| 3,598,113 | 8/1971 | Moore | 128/11 |
| 3,609,340 | 9/1971 | Habro |  |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 3,986,854 | 10/1976 | Scrivo et al. | 128/11 X |
| 4,037,588 | 7/1977 | Heckele | 128/11 |
| 4,112,933 | 9/1978 | Moses | 128/11 |
| 4,114,187 | 9/1978 | Uke | 362/158 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/11 |
| 4,314,551 | 2/1982 | Kadell | 128/11 |
| 4,320,745 | 3/1982 | Bhitiyakul et al. | 128/11 |
| 4,337,761 | 7/1982 | Upsher | 128/11 |
| 4,384,570 | 5/1983 | Roberts | 128/11 |
| 4,406,280 | 9/1983 | Upsher | 128/11 |
| 4,437,458 | 3/1984 | Upsher | 128/11 |
| 4,517,964 | 5/1985 | Upsher | 128/11 |
| 4,527,223 | 7/1985 | Maglica | 362/187 |
| 4,527,553 | 7/1985 | Upsher | 128/11 |
| 4,556,052 | 12/1985 | Muller | 128/11 |
| 4,557,256 | 12/1985 | Bauman | 128/11 |
| 4,565,187 | 1/1986 | Soloway | 128/11 |
| 4,570,614 | 2/1986 | Bauman | 128/11 |
| 4,573,451 | 3/1986 | Bauman | 128/11 |
| 4,574,784 | 3/1986 | Soloway | 128/11 |
| 4,583,528 | 4/1986 | Bauman | 128/11 |
| 4,592,343 | 6/1986 | Upsher | 128/11 |
| 4,607,623 | 8/1986 | Bauman | 128/11 |

Primary Examiner—William H. Grieb
Attorney, Agent, or Firm—William W. Haefliger

[57] ABSTRACT

A laryngoscope, has a blade and a hollow body including a handle and a cap, and also includes:
  (a) the handle adapted to receive a dry cell or cells, the handle having an open end,
  (b) the cap telescopically and removably interfitting the handle to close its open end, and a seal sealing off between the cap and handle,
  (c) a sealed window carried by the cap to pass light from a light source within the body to a predetermined zone at the cap exterior, whereby such light may be transmitted along the blade removably attached to the cap,
  (d) a flexible barrier carried by the cap to be deflected by the blade upon its attachment to the cap, the barrier sealing off between the cap interior and exterior,
  (e) and circuitry including a motion transmitting element to be deflected within the hollow body in response to barrier deflection to establish an ON condition of the circuitry for transmitting current from the dry cell to the light source.

28 Claims, 14 Drawing Figures

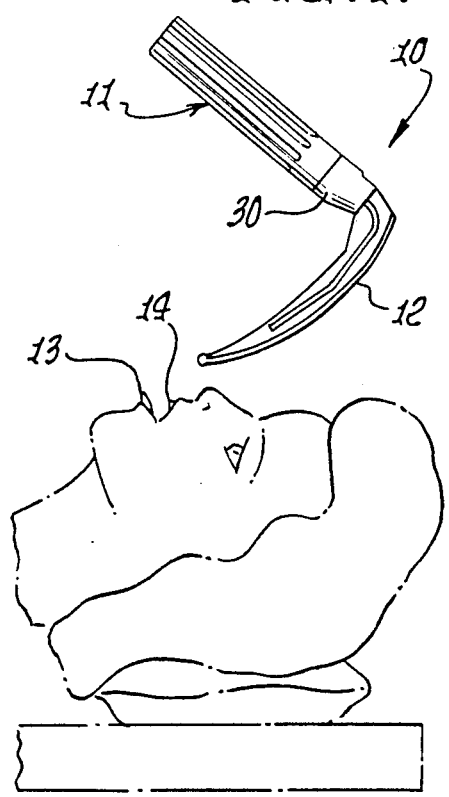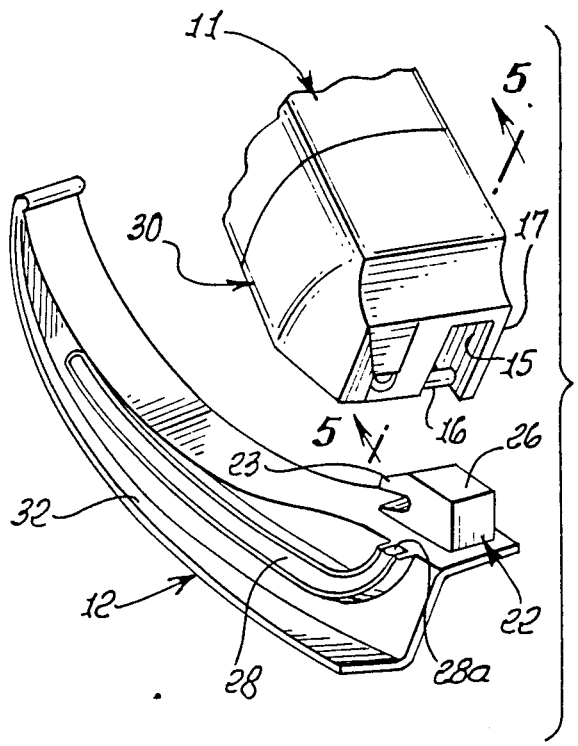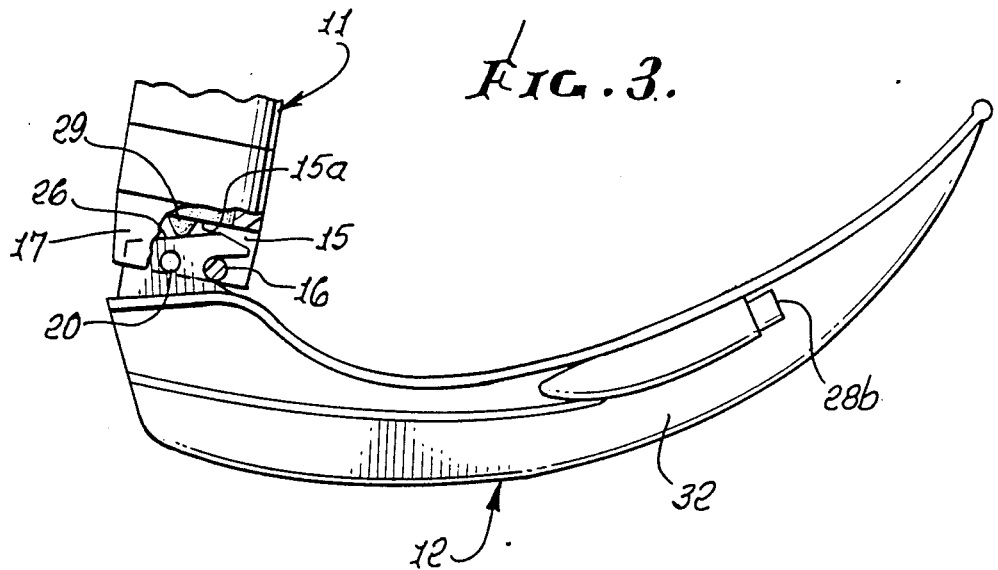

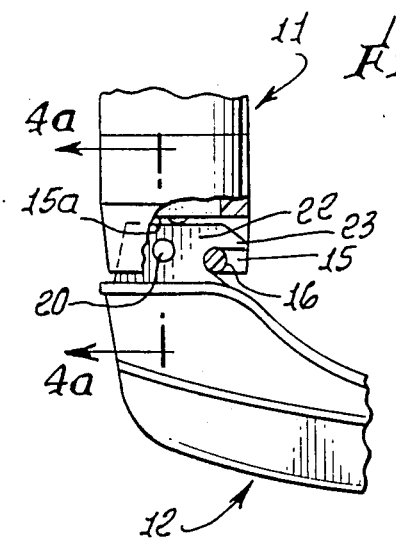
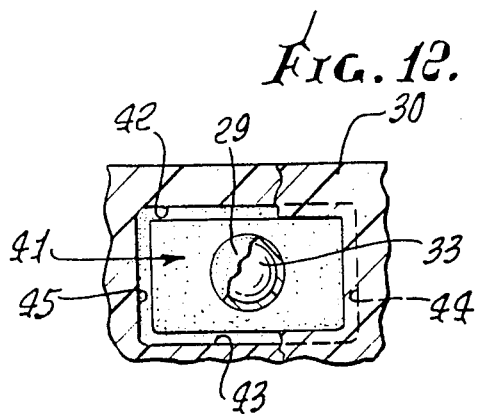
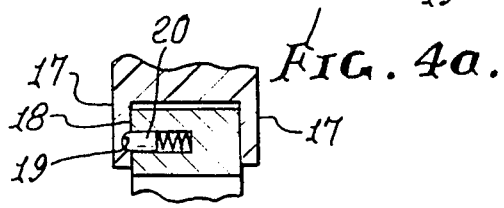
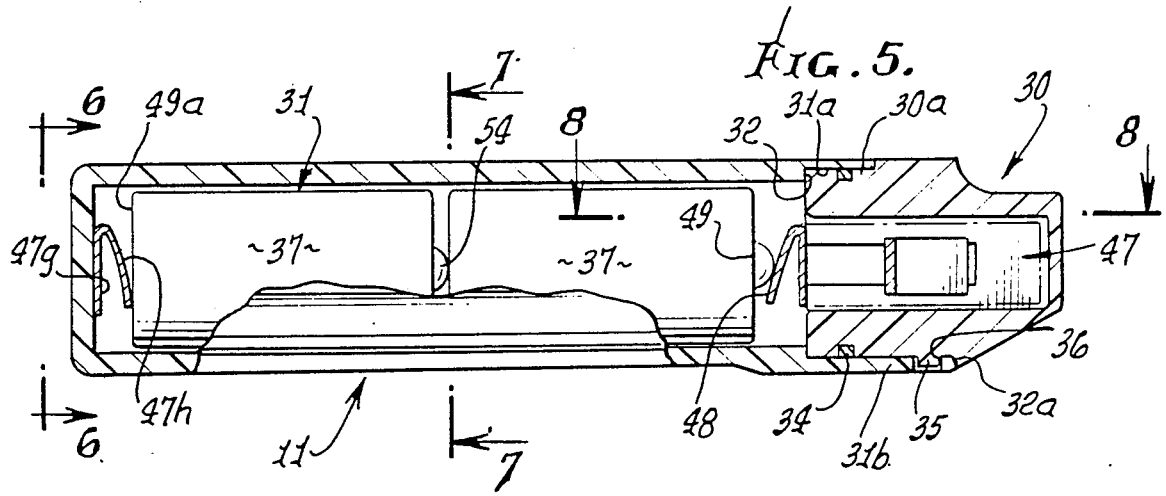
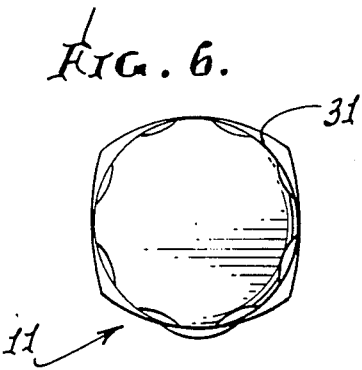
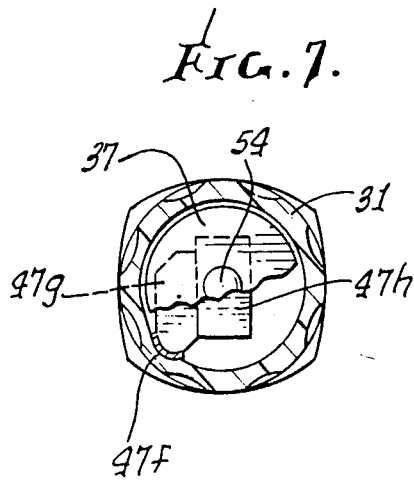

SUBMERGIBLE LARYNGOSCOPE BATTERY HOUSING

BACKGROUND OF THE INVENTION

This invention generally relates to examining devices such as laryngoscopes and particularly to an improved submersible device of this type.

Laryngoscopes generally comprise a blade and a cooperating handle which are connected together in an L-shaped configuration. The hollow handle normally serves as an enclosure for a power supply such as one or more dry cells which are adapted to energize a light bulb. The light from the bulb passes to the distal end of the blade to illuminate the patient's mouth and larynx during the examination thereof by medical personnel. A surface on the blade is used to press against the tongue and mandible of a patient's tongue from obstructing the visual examination of the larynx by medical personnel.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures and the opposite blade surface is positioned opposing the upper front teeth of the patient.

It becomes desirable to provide a re-usable blade and handle which must be cleaned thoroughly after use since fluid from the patient's mouth area can contaminate the handle. However, washing of the handle presents the problem of fluid gaining access to the power supply, i.e. dry cells, within the handle hollow, as via one or both ends of the handle. This is a particular problem when the light bulb is carried at the end of the handle to which the blade attaches, as cleaning fluid can leak past the bulb into the handle to cause bulb circuit malfunction.

SUMMARY OF THE INVENTION

It is a major object of the invention to provide a solution to the above problem, through provision of a fluid or liquid submersible laryngoscope including a hollow handle to contain power supply means, a blade to be inserted into a patient's mouth, and means to removably attach the blade to an end portion of the handle in a substantially L-shape configuration, the improvement comprising (a) the handle adapted to receive dry cell means, the handle having an open end, (b) the cap telescopically and removably interfitting the handle to close said open end, and means sealing off between the cap and handle, (c) means carried by the cap to pass light from a light source within cap body means to a predetermined zone at the cap exterior, whereby such light may be transmitted along the blade removably attached to the cap, (d) a flexible barrier carried by the cap to be deflected by the blade upon its attachment to the cap, the barrier sealing off between the cap interior and exterior, (e) and circuit means including a motion transmitting element to be deflected within the hollow body means in response to such barrier deflection to establish an ON condition of the circuit means for transmitting current from the battery means to the light source.

As will appear, the handle, cap or blade, or combination thereof may consist of light-weight molded plastic material interfitting in such manner as to preserve laryngoscope functions while preventing fluid access to the cap and handle interior during washing; the cap may have an end wall defining a light opening, such light passing means sealingly attached to said wall to pass light from said opening, while blocking fluid access from the cap exterior via the opening to the interior of the cap; and the cap may have a wall defining an opening across which the flexible barrier extends to block fluid access from the cap exterior via said opening to the interior of the cap. In this regard, the sub-chamber in which the light source and flexible barrier are contained may be substantially rectangular, for purposes as will appear.

Additional objects include the provision of circuit means including a battery receptacle received endwise into said hollow handle, and into the cap, to interfit same; and the receptacle may comprise a molded plastic unit having electrically conductive plating thereon, the plating having at least two sections which are not electrically connected, one section electrically connectible to a dry cell plus terminal, and the other section electrically connectible to a dry cell negative terminal. The motion transmitting element may be integral with the receptacle and positioned to extend proximate said flexible barrier to be deflected thereby, and switch terminals carried by the receptacle to be closed together in response to said deflection of the motion transmitting element.

These and other objects and advantages of the invention, as well as the details of an illustrative embodiment, will be more fully understood from the following specification and drawings, in which:

DRAWING DESCRIPTION

FIG. 1 is a side elevational view of a laryngoscope at the time of use on a patient, and which embodies features of the invention;

FIG. 2 is a perspective view of the laryngoscope blade and handle end, prior to their assembly;

FIG. 3 is a side elevational view, partially in section, of a laryngoscope, with the blade in ready oosition;

FIG. 4 is a partial side elevational view, partially in section, of the laryngoscope, with blade in operative position;

FIG. 4a is a cross sectional view taken along lines 5—5 shown in FIG. 4;

FIG. 5 is a section taken in elevation showing details of the handle portion of the laryngoscope;

FIG. 6 is an end view taken in elevation on lines 6—6 of FIG. 5;

FIG. 7 is a section taken in elevation on lines 7—7 of FIG. 5;

FIG. 12 is a fragmentary section taken on lines 12—12 of FIG. 8; and

DETAILED DESCRIPTION

Figure 8:
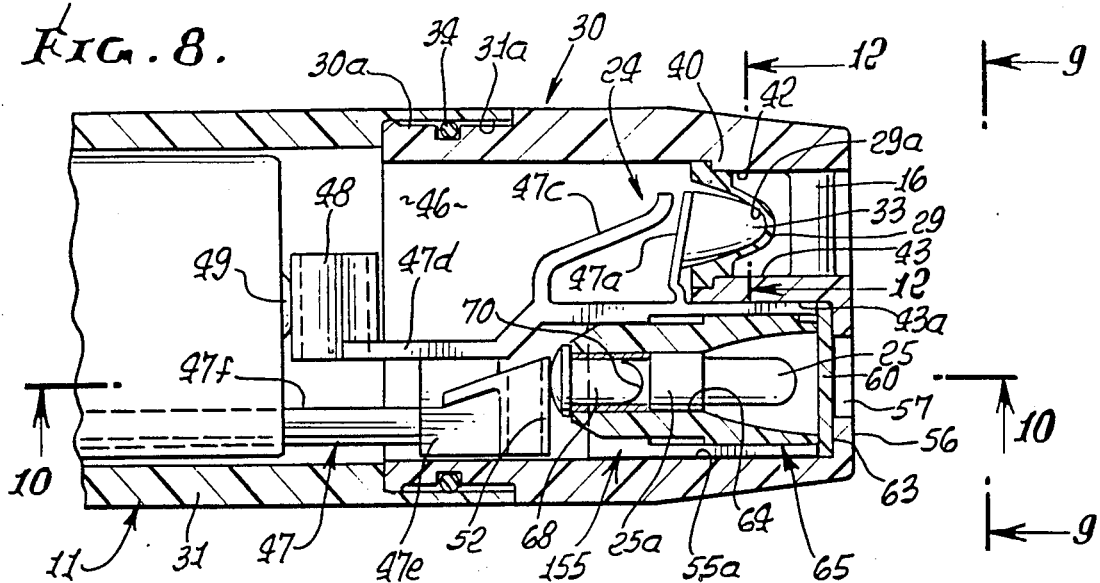
FIG. 8 is an enlarged plan view section taken on lines 8—8 of FIG. 5.

The laryngoscope 10, which comprises a handle 11 and blade 12, is utilized to depress the patient's tongue and mandible 13. Frequently, the patient's front teeth 14 are used as a fulcrum for the blade 12, in order to more completely expose the larynx during examination, and to insert an endotracheal tube.

In order to couple the blade 11 to the handle 12, and as shown in FIGS. 2–4, the upper end of the handle 11 has an open channel 15 provided with a pivot rod 16 extending between flanges 17. The inner side of one flange has a groove or dimple 19 adapted to seat detent 20 projecting at one side surface 18 of a boot shaped appendage on the blade.

The boot shaped appendage 22 interfits into the open channel 15 and is mounted therein in a pivotal fashion. The front end 23 of the boot shaped appendage 22 is hooked under the pivot rod 16 during the pivotal mounting thereof, in a conventional fashion. To mount the blade onto the handle 11, the appendage 22 of the blade 12 is inserted into the open top channel 15 with a pivotal motion so that the front end 23 rotates under the pivot rod 16 i.e., from FIG. 3 to FIG. 4 condition. The detent 20 moves into engagement with the groove 19 provided in the surface 18, to thereby snap-retain the appendage 22 in firm interfit with the channel and pivot rod 16, as the blade moves from ready position, as shown in FIG. 3, to fixed position seen in FIG. 4.

A light such as an incandescent bulb 25 is provided at the end of the handle proximate the blade to be activated when a light switch 24 is closed by a motion transmitting element 33, as when pushed by bottom surface 26 of appendage or boss 22, via a flexible sealing barrier 29. As snown in FIG. 3, when the blade 12 is initially mounted on the handle 11, the blade 11 is in a ready position on the handle 12 but the bottom surface 26 of the appendage 22 does not activate, i.e. depress,the light switch. Further rotation of the blade 12 causes the detent 20 to engage the groove 19, and to thereby lock the blade 12 in an operating position and simultaneously therewith to cause metallic bottom surface 26 to depress, i.e. activate the light switch 24, which in turn energizes the light source 25.

As best shown in FIGS. 2–4, light is directed from the light source 25 (see FIG. 80 to ensure the proper illumination of a patient's mouth and larynx when the laryngoscope is being used. The light source or bulb 25 is located near the bottom wall 15a of channel 15 so that, when the blade 12 is rotated into its final operating position, not only is switch 24 engaged, but also the energized bulb directs light into the end 28a of the light pipe or duct 28 carried by the blade and conducting light to the light emitting end 28b directing light forwardly from a channel in blade web 32. Duct 28 may be of optical fiber.

The switch 24 and bulb 25 are both contained in a lightweight plastic cap 30 which fits telescopically onto the lightweight plastic handle body 31, as better seen in FIGS. 5 and 8. As thereshown, the cap 30 has a skirt 30a received into the body bore 31a, to shoulder at 32 and 32a. O-ring seal 34, typically of rubber and carried by skirt 30a, seals off between that skirt and bore 31a. A boss 35 integral with the skirt removably fits or snaps into an opening 36 in the body wall 31b, as shown, to lock the cap in position. Accordingly, the open end of body 31 is closed by the cap. Body 31 receives dry cells 37 that supply electrical energy to the incandescent bulb when switch 24 is closed.

Figure 13:
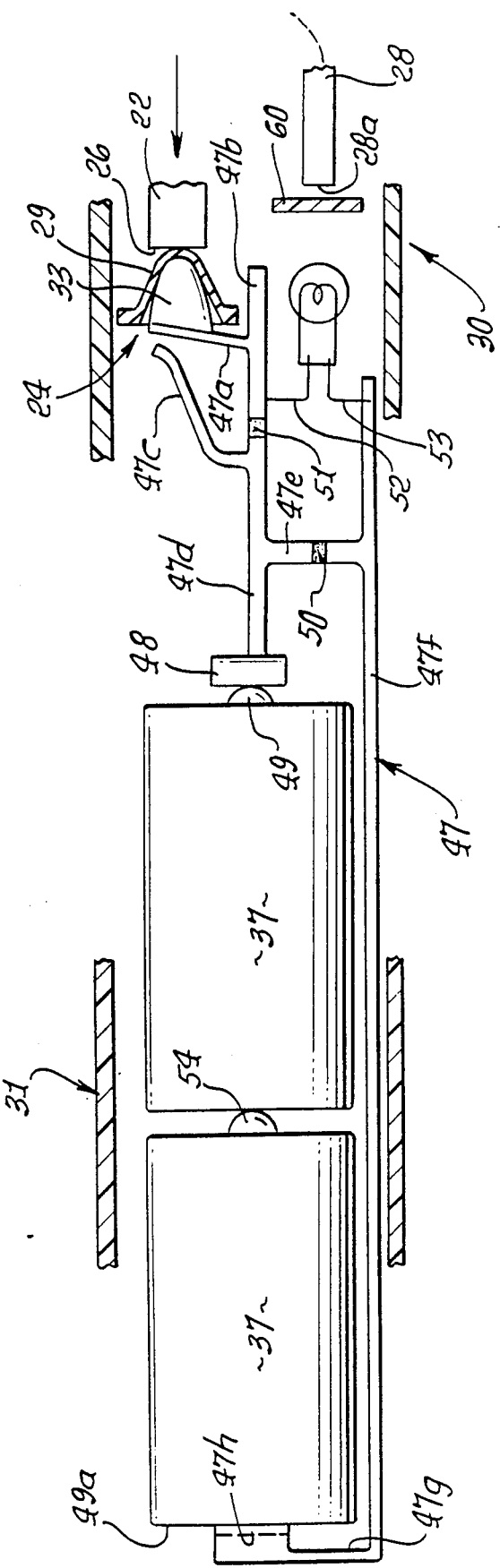
FIG. 13 is a schematic view of circuitry.

Reference is now made to FIG. 13, showing partially schematically, the integration of circuit means, dry cells, element 33, switch 24, barrier 29, pusher 22 on the blade, and bulb 25. The element 33 may with unusual advantage comprise a nose-shaped part projecting into a corresponding recess 29a formed by the elastomeric barrier 29 which is peripherally retained in position by the cap, as shown at 40 in FIG. 8. In that view, and in FIG. 12 the barrier 29 and part 33 are shown to extend within a sub-chamber 41 formed by cap walls 42–45, and the barrier seals off access to the interior 46, via sub-chamber 41. The latter has a substantially rectangular cross section to interfit part 47 to be described.

Returning to FIG. 13, the part 33 may with unusual advantage be integrally molded with an elongated holder or bracket 47 having components 47a–47h, these being identified further as follows:

47a—arm supporting part 33 and adapted to bend as blade part 22 pushes against barrier 29 to deflect part 33 leftwardly and close the switch, 47b—support for arm 47a and fitting cap wall 43a, 47c—switch terminal to be engaged by part 33, to close the switch, 47d—projection that supports terminal 48 engaged by battery contact 49, 47e—support arm that supports 47b, 47c and stretch 47f, 47f—base stretch that may support batteries 37 to form a sub-assembly insertible into the body 31 and into cap 30, 47g—connects base stretch 47f to terminal 47h, 47h—terminal that engages the left battery contact end face 49a.

The said bracket 47 and part 33 thereof may be molded of lightweight strong plastic material and coated with a thin conductive metallic layer, such as silver, except for regions 50 and 51. As a result, when part 33 closes against switch terminal 47c, electrical current flows along the following path: from battery contact 49 through coatings on 47d, 47c 33, and 47b to conductor 52 to bulb 25, then through conductor 53 to coatings on parts 47f, 47g and 47h to the battery contact face 49a. Batteries 37 are of course themselves in end-to-end conductive contact at 54.

Figure 9:
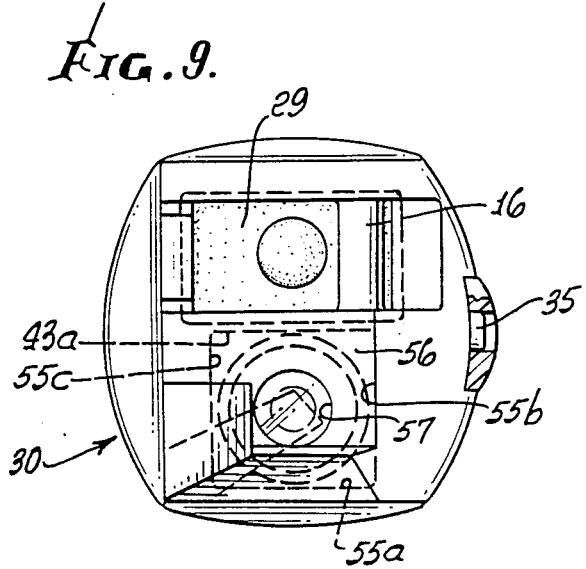
FIG. 9 is an end view taken in elevation on lines 9—9 of FIG. 8.

Referring now to FIGS. 5, 8 and 9, the cap 30 also defines a second sub-chamber 55 which may be rectangular in outline, as defined by walls 43a, 55a, 55b and 55c. End wall 56 of sub-chamber 55 contains an aperture 57 to pass light from bulb 25 to optical fiber light pipe 28, via the end thereof 28a, as previously described. A light passing means in the form of window 60 serves to transmit light from the bulb and reflector 60a toward and onto the end 28a of optical light pipe 28, as also shown in FIG. 13. Window 60 may consist of plastic material and be bonded to the inner surface of end wall 56 at 63, to seal-off the rectangular outline sub-chamber 55 from the exterior, whereby the interior 46 of the handle is kept free from exterior moisture of liquid.

As also shown in FIG. 8, the bulb base 25a is received in bore 64 of a bulb holder 65, which in turn is received in a bracket 155 that fits closely to walls 55a–55c, and also to part 47b of the receptacle 47. Conductor 53 indicated systematically in FIG. 13 may take the form of conductive holder 155 in FIGS. 8 and 9, and 52 in FIG. 13 may take the form in FIGS. 8 and 10 of a tab integrally molded with the receptacle 47, and projecting to engage an insert terminal 68 which in turn engages the bulb contact 70.

Figure 11:
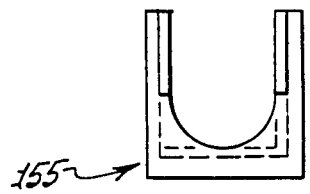
FIG. 11 is a section on lines 11—11 of FIG. 10.
Figure 10:
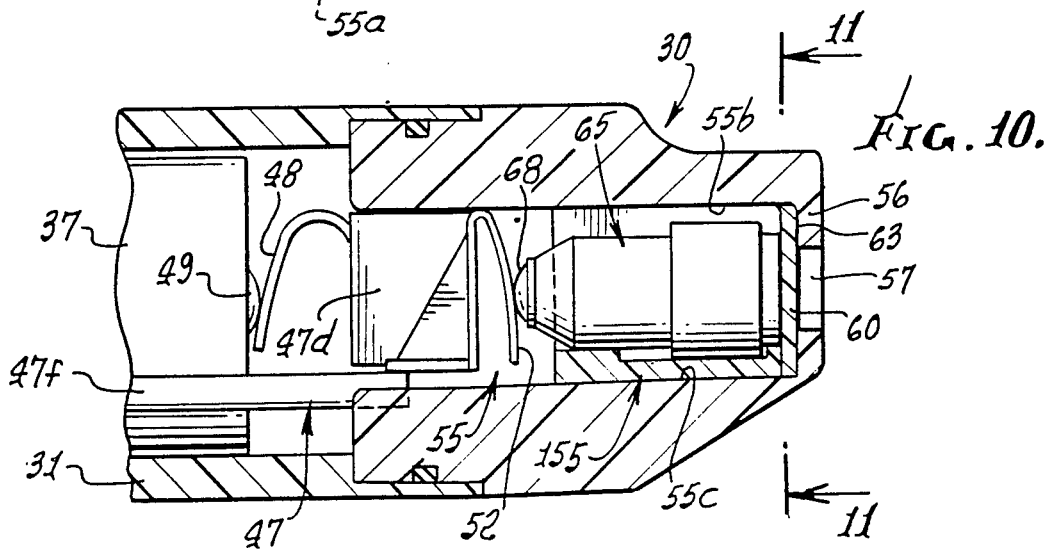
FIG. 10 is a section on lines 1—10 of FIG. 8.

In the views shown in FIGS. 10 and 11, the bracket 155 is shown as U-shaped to receive holder 65. Its exterior is rectangular to fit in the cap rectangular sub-chamber 55.

I claim:

1. In a laryngoscope, having a blade and hollow body means including a handle and a cap, the combination comprising
   (a) the handle adapted to receive dry cell means, the handle having an open end,
   (b) the cap telescopically and removably interfitting the handle to close said open end, and means sealing off between the cap and handle,
   (c) means carried by the cap to pass light from a light source within said body means to a predetermined zone at the cap exterior, whereby said light may be transmitted along the blade removably attached to the cap,
   (d) a flexible barrier carried by the cap to be deflected by the blade upon its attachment to the cap, the barrier sealing off between the cap interior and exterior,
   (e) and circuit means including a motion transmitting element to be deflected within the hollow body means in response to said barrier deflection to establish an ON condition of the circuit means for transmitting current from said dry cell means to said light source.

2. The combination of claim 1 wherein at least one of said handle, cap and blade consist of molded plastic material.

3. The combination of claim 1 wherein at least two of said handle, cap and blade consist of molded plastic material.

4. The combination of claim 1 wherein each of said handle, cap and blade consists of molded plastic material.

5. The combination of claim 1 wherein said cap has a wall defining a light opening, said light passing means sealingly attached to said wall to pass light from said opening, while blocking fluid access from the cap exterior via said opening to the interior of the cap.

6. The combination of claim 1 wherein said cap has a wall defining an opening across which said flexible barrier extends to block fluid access from the cap exterior via said opening to the interior of the cap.

7. The combination of claim 5 wherein said cap has a wall defining a second opening across which said flexible barrier extends, to block fluid access from the cap exterior via said second opening to the interior of the cap.

8. The combination of claim 6 wherein said opening across which the flexible barrier extends is substantially rectangular in cross section.

9. The combination of claim 5 wherein said light opening is substantially rectangular in cross section.

10. The combination of claim 7 wherein each of said openings is substantially rectangular in cross section.

11. The combination of claim 1 wherein said circuit means includes a battery receptacle received endwise into said hollow handle, and into said cap, to interfit same.

12. The combination of claim 11 wherein said receptacle comprises a molded plastic unit having electrically conductive plating thereon, the plating having at least two sections which are not electrically connected, one section electrically connectible to a dry cell plus terminal, and the other section electrically connectible to a dry cell negative terminal.

13. The combination of claim 11 wherein said motion transmitting element is integral with said receptacle and positioned to extend proximate said flexible barrier to be deflected thereby, and switch terminals carried by said receptacle to be closed together in response to said deflection of the motion transmitting element.

14. The combination of claim 12 wherein said motion transmitting element is integral with said receptacle and positioned to extend proximate said flexible barrier to be deflected thereby, and switch terminals are carried by said receptacle to be closed together in response to said deflection of the motion transmitting element.

15. The combination of claim 1 wherein including a light pipe carried by the blade, and having a light receiving terminus in the path of light passed by said light passing means when the blade is attached to the cap.

16. The combination of claim 15 wherein said light passing means comprises a window transmitting light toward said terminus when the blade is attached to the cap.

17. The combination of claim 15 wherein said light pipe comprises a fiber optics element that extends lengthwise along said blade which has lengthwise curvature.

18. The combination of claim 16 wherein said window is sealingly bonded to an end wall defined by the cap.

19. The combination of claim 1 wherein said cap defines two substantially rectangular sub-chambers one receiving said barrier and motion transmitting element, and the other receiving said light source, a light reflector, and a window sealingly engaging an end wall defined by the cap.

20. The combination of claim 19 including means releasably locking the cap to said handle.

21. The combination of claim 1 wherein said circuit means includes a conductive clip connecting the dry cell means with the light source.

22. In a fluid submersible laryngoscope including a hollow handle to contain power supply means, a blade to be inserted into a patient's mouth, and means to removably attach the blade to an end portion of the handle in a substantially L-shaped configuration, the improvement comprising
   (a) a cap carried by the handle at said end portion of the handle, the cap having a first zone to receive a light bulb, and a second zone to receive a switch which, when closed, completes a circuit between the power supply and the bulb,
   (b) and fluid sealing means between the cap and handle to block access of external fluid into the hollow handle, and cap, whether or not the blade is attached to the handle, and when the handle is submerged in fluid.

23. The improvement of claim 22 including a window carried by the cap to pass light from the bulb and a reflector associated therewith to optical fiber means carried by the blade.

24. The improvement of claim 22 including a sealing diaphragm carried by the cap to deflect during motion transmission from the blade to said switch when the blade is attached to the handle.

25. The improvement of claim 24 including a pivot associated with the cap and via which the blade is rotatably attachable to the cap and handle, as said diaphragm is deflected.

26. The improvement of claim 23 wherein said cap defines a second zone to receive the switch, the first and second zones located in side-by-side relation, only said diaphragm separating said second zone from the exterior of the cap.

27. In a laryngoscope, having a blade and hollow body means including a handle having an end wall, the combination comprising
   (a) the handle adapted to receive dry cell means,
   (b) an end wall closing the hollow body at an end of the handle,
   (c) a light source within said end wall to transmit light to a predetermined zone at the handle exterior, whereby said light may be transmitted along the blade removably attached to said end wall,
   (d) a flexible barrier carried by the body means to be deflected by the blade upon its attachment to the end wall, the barrier sealing off between the body means interior and exterior,
   (e) and circuit means including a motion transmitting element to be deflected within the hollow body means in response to said barrier deflection to establish an ON condition of the circuit means for transmitting current from said battery means to said light source.

28. The combination of claim 27 wherein said handle is longitudinally elongated, and said barrier and light source are laterally spaced apart at said end of the handle.

* * * * *